US007052852B1

(12) United States Patent
Mullan et al.

(10) Patent No.: US 7,052,852 B1
(45) Date of Patent: May 30, 2006

(54) CD45 ISOFORM ALTERATION IN CD4+ T CELLS AS A POTENTIAL DIAGNOSTIC MARKER IN ALZHEIMER'S DISEASE

(75) Inventors: Michael J. Mullan, Tampa, FL (US); Terrence C. Town, Tampa, FL (US); Jun Town Tan, Tampa, FL (US)

(73) Assignee: Roskamp Research, LLC, Sarasota, FL (US)

( * ) Notice: Subject to any disclaimer, the term of this patent is extended or adjusted under 35 U.S.C. 154(b) by 19 days.

(21) Appl. No.: 10/426,301

(22) Filed: Apr. 30, 2003

Related U.S. Application Data (63) Continuation of application No. 09/986,471, filed on Nov. 8, 2001, now abandoned.

(60) Provisional application No. 60/246,967, filed on Nov. 8, 2000.

(51) Int. Cl.
*C12Q 1/68* (2006.01)
*G01N 33/53* (2006.01)

(52) U.S. Cl. .......................... 435/7.1; 435/6; 435/7.21; 435/7.24; 435/91.2; 436/501

(58) Field of Classification Search ................ 435/7.1, 435/7.21, 7.24
See application file for complete search history.

(56) References Cited

U.S. PATENT DOCUMENTS 5,120,642 A * 6/1992 Schlossman et al. ...... 435/7.24

OTHER PUBLICATIONS

Hossein Ghanbari et al., Biochemical Assay for AD7C-NTP in Urine as an Alzheimer's Disease Marker, Journal of Clinical Laboratory Analysis, vol. 12, pp. 285-288 (1998).
Kasra Ghanbari et al., A Sandwich Enzyme Immunoassay for Measuring AD7C-NTP as an Alzheimer's Disease Marker: AD7C Test, Journal of Clinical Laboratory Analysis, vol. 12, pp. 223-226 (1998).
Masanori Utsuyama et al., Different Age-Change in the Numbers of CD4+CD45RA+ And CD4+CD29+ T Cell Subsets in Human Peripheral Blood, Mechanisms of Ageing and Development, vol. 63 (1992), pp. 57-68.
Tero Tapiola et al., Relationship between apoE Genotype and CSF β-amyloid (1-42) and Tau in Patients with Probable and Definite Alzheimer's Disease, Neurobiology of Aging, vol. 21 (2000), pp. 735-740.
Jun Tan et al., Activation of Microglial Cells by the CD40 Pathway: Relevance to Multiple Sclerosis, Journal of Neuroimmunology, vol. 97 (1999), pp. 77-85.
Eric T. Poehlman et al., Energy Expenditure, Energy Intake, and Weight Loss in Alzheimer Disease[1-4], Am J Clin Nutr 2000, vol. 72 (suppl), pp. 650S-655S.

I.Skoog et al., A Population Study on Blood-Brain Barrier Function in 85-Year Olds, NEUROLOGY, vol. 50, Apr. 1998, pp. 966-971.
Mikio Shoji, Combination Assay of CSF Tau, Aβ1-40 and Aβ1-42(43) as a Biochemical Marker of Alzheimer's Disease, Journal of the Neurological Sciences vol. 158 (1998), pp. 134-140.
A. M. Saunders PhD et al., Association of Apolipoprotein E Allele ∈4 with Late-Onset Familial and Sporadic Alzheimer's Disease, NEUROLOGY, vol. 43, Aug. 1993, pp. 1467-1472.
A. M. Saunders et al., Specificity, Sensitivity, and Predictive Value of Apolipoprotein-E Genotyping for Sporadic Alzheimer's Disease, The Lancet, vol. 348, Jul. 13, 1996, pp. 90-93.
Allen D. Roses MD, Apolipoprotein E Genotyping in the Differential Diagnosis, Not Prediction, of Alzheimer's Disease, Annals of Neurology, vol. 38, No. 1, Jul. 1995, pp. 6-14.
R. Motter, MPH et al., Reduction of β-Amyloid Peptide$_{42}$ in the Cerebrospinal Fluid of Patients with Alzheimer's Disease, Annals of Neurology, vol. 38, No. 4, Oct. 1995, pp. 643-648.
Bruce H. Price MD, et al., Neuropsychological Patterns and Language Deficits in 20 Consecutive Cases of Autopsy-Confirmed Alzheimer's Disease, Arch Neurol, vol. 50, No. 9, Sep. 1993, pp. 931-937.
Judes Poirier et al., Apolipoprotein E Polymorphism and Alzheimer's Disease, The Lancet, vol. 342, No. 8873, Sep. 18, 1993, pp. 697-699.
Guy McKhann, MD et al., Clinical Diagnosis of Alzheimer's Disease: . . . , NEUROLOGY, vol. 34, No. 7, Jul. 1984, pp. 939-944.
Richard Mayeux MD et al., Utility of the Apolipoprotein E Genotype in the Diagnosis of Alzheimer's Disease, The New England Journal of Medicine, vol. 338, No. 8, Feb. 19, 1998, pp. 506-511.
R. Mayeux, Evaluation and Use of Diagnostic Tests in Alzheimer's Disease, Neurobiology of Aging, vol. 19, No. 2, (1998), pp. 139-143.
Zaven S. Khachaturian, PhD, Diagnosis of Alzheimer's Disease, Arch Neurol, vol. 42, No. 11, Nov. 1985, pp. 1097-1105.

(Continued)

*Primary Examiner*—Lorraine Spector
*Assistant Examiner*—Jon M. Lockard
(74) *Attorney, Agent, or Firm*—The Webb Law Firm (57) ABSTRACT

Methods for assessing the risk of developing Alzheimer's Disease (AD), for diagnosing AD, and for measuring the progression of AD in a patient by determining CD45 isoform expression of blood cells obtained from the patient. The methods of the invention include determining CD45 isoform expression by cytometric analysis, quantitative Western immunoblotting, or quantitative RT-PCR or combinations thereof.

5 Claims, 3 Drawing Sheets

OTHER PUBLICATIONS

Rajesh N. Kalaria, Cerebrovascular Degeneration Is Related to Amyloid-β Protein Deposition in Alzheimer's Disease, Annals New York Academy of Sciences, pp. 263-271, (Sep. 26, 1997).

Ikeda T. Yamamoto et al., Immune System-Associated Antigens on the Surface of Peripheral Blood Lymphocytes in Patients with Alzheimer's Disease, ACTA Psychiatrica Scandinavica, pp. 444-448, (Jun. 1991).

F. Hulstaert, MD et al., Improved Discrimination of AD Patients Using β-Amyloid$_{(1-42)}$ and Tau Levels in CSF, Neurology, vol. 52, May 1999, pp. 1555-1562.

G. R. Hue et al., Peripheral Blood Lymphocyte Subset Distribution and Function in Patients with Alzheimer's Disease and Other Dementias, Aust NZ J Med 1995; vol. 25, pp. 212-217.

Kevin Flurkey et al., Memory T Lymphocyte Hyporesponsiveness to Non-Cognate Stimuli: A Key Factor in Age-Related Immunodeficiency, (Apr. 1992) Eur. J. Immunol. 22(4) 931-935.

Ron Brookmeyer, PhD et al., Projections of Alzheimer's Disease in the United States and the Public Health Impact of Delaying Disease Onset, American Journal of Public Health, Sep. 1998, vol. 88, No. 9, pp. 1337-1342.

Philip R. Wenham et al., Apolipoprotein E Genotyping by One-Stage PCR, The Lancet, vol. 337, May 11, 1991, pp. 1158-1159.

Stephen W. Hunt III et al., T-Lymphocyte Interactions with Endothelium and Extracellular Matrix, Crit Rev Oral Biol Med, 7(1), (1996), pp. 59-86.

R.C. Petersen, Mild Cognitive Impairment: Transition Between Aging and Alzheimer's Disease, NEUROLOGIA, vol. 15, No. 3, Marzo 2000, pp. 93-101.

* cited by examiner

CD45 ISOFORM ALTERATION IN CD4+ T CELLS AS A POTENTIAL DIAGNOSTIC MARKER IN ALZHEIMER'S DISEASE

CROSS-REFERENCE TO RELATED APPLICATIONS

This application is a continuation of application Ser. No. 09/986,471; now abandoned filed Nov. 8, 2001; now abandoned which claims the benefit of provisional application Ser. No. 60/246,967; filed Nov. 8, 2000, which is hereby incorporated by reference in its entirety.

FIELD OF THE INVENTION

The present invention relates to methods of assessing the risk of developing, of diagnosing, or of measuring the progression of Alzheimer's disease in a patient. More specifically, the present invention relates to methods of assessing, the risk of developing, of diagnosing, or of measuring the progression of Alzheimer's disease by measuring CD45 isoform expression in blood cells.

BACKGROUND OF THE INVENTION

Alzheimer's disease (AD) is the most commonly reported dementing illness, producing a progressive loss of memory and other higher cognitive functions, eventually leading to death. AD may only be definitively diagnosed by pathological observation of both senile plaques and neurofibrillary tangles. McKhann G, Drachman D, Folstein M, Katzman R, Price D, and Stadlan E M, *Clinical Diagnosis of Alzheimer's Disease: Report of the NINCDS-ADRDA Work Group under the Auspices of Department of Health and Human Services Task Force on Alzheimer's Disease*, Neurology 34:939–944 (1984); Khachaturian Z S, *Diagnosis of Alzheimer's disease*, Arch Neurol 42:1097–1105 (1985). Current methods of diagnosing AD at the early stages rely primarily on directly assessing patients and interviewing family members, often supplemented by neuroimaging studies. However, at specialist centers, evaluating for AD (clinical neuropsychometric and neuroradiological workups) takes several hours of the patient's and clinician's time; a quick and easy diagnostic test which would dramatically reduce time is still needed. Additionally, an early biological marker of AD would be useful so that treatments a slow the progression of AD or delay the onset of AD could be administered in the early stages of the disease, thereby optimizing therapeutic benefit. Brookmeyer R, and Zeger S, *Statistical issues in prevention and therapeutic trials of Alzheimer's disease*, Alzheimer Dis Assoc Disord 10:27–30 (1996); Brookmeyer R, Gray S, and Kawas C, *Projection of Alzheimer's disease in the United States and the public health impact of delaying disease onset*, Am J Publi Health 88:1337–1342 (1998). Consequently, a biomarker of AD that would allow for a rapid, simple, inexpensive, and minimally invasive substitute for the standard diagnostic assessment is still needed.

Most of the currently available commercial tests for diagnosing Alzheimer's Disease (AD) are Cerebral Spinal Fluid (CSF)-based, like ADmark tau/A$\beta_{1-42}$ and Nymox AD7C-NTP and, therefore, are somewhat invasive. Mayeux R, *Evaluation and use of diagnostic tests in Alzheimer's disease*, Neurobiol Aging 19:139–143 (1998). A test which combines CSF tau and A$\beta_{1-42}$ measurements and utilizes cutoff values which best separate AD cases from others has sensitivity values ranging between 50 and 85% and specificity values between 86 and 96%. Motter R, Vigo-Pelfrey C, and Kholodenko D, *Reduction of β-amyloid peptide$_{42}$ in the cerebrospinal fluid of patients with Alzheimer's disease*, Annals Neurology 38:643–648(1995); Shoji M, Matsubara E, Kanai M, Watanabe M, Nakamura T, Tomidokoro Y, Shizuka M, Wakabayashi K, Igeta Y, Ikeda Y, Mizushima K, Amari M, Ishiguro K, Kawarabayashi T, Harigaya Y, Okamoto K, and Hirai S, *Combination assay of CSF tau, A beta 1–40 and A beta 1–42(43) as a biochemical marker of Alzheimer's disease*, J Neurol Sci 158:134–140 (1998); Tapiola T, Pirttila T, Mehta P D, Alafuzofff I, Lehtovirta M, and Soininen H, *Relationship between apoE genotype and CSF beta-amyloid (1–42) and tau in patients with probable and definite Alzheimer's disease*, Neurobiol Aging 21:735–740 (2000); Hulstaert F, Blennow K, Ivanoiu A, Schoonderwaldt H C, Riemenschneider M, De Deyn P P, Bancher C, Cras P, Wiltfang J, Mehta P D, Iqbal K, Pottel H, Vanmechelen E, and Vanderstichele H, *Improved discrimination of AD patients using beta-amyloid (1–42) and tau levels in CSF*, Neurology 52:1555–1562 (1999). However, critics have previously criticized the combined tau/A$\beta_{1-42}$ test for its high false negative rate (which is due to AD cases with low CSF tau levels), and lack of diagnostic value when both tau/A$\beta_{1-42}$ values are either high or low (approximately ⅓ of subjects). Ghanbari K, and Ghanbari H A, *A sandwich enzyme immunoassay for measuring AD7C-NTP as an Alzheimer's disease marker*: AD7C test, J Clin Lab Anal 6:379:383 (1998).

Another test, the AD7C-NTP biomarker test (Nymox corporation), is based on a raised neural thread protein in AD brains and CSF (although a large clinical study for the efficacy of measurement in urine is underway). Ghanbari K, and Ghanbari H A, *A sandwich enzyme immunoassay for measuring AD7C-NTP as an Alzheimer's disease marker*: AD7C test. J Clin Lab Anal 6:379:383 (1998); Ghanbari H, Ghanbari K, and Beheshti I, *Biochemical assay for AD7C-NTP in urine as an Alzheimer's disease marker*, J Clin Lab Anal 12:285:288 (1998). As a CSF-based test, the sensitivity and specificity were high (89%) for AD compared to age-matched, non-demented controls. Both the ADmark tau/A$\beta_{1-42}$ and the Nymox AD7C-NTP tests were developed in known cases of dementia versus non-demented controls. A predictive test for cognitive impairment would also be useful, as subjects with cognitive impairment frequently progress to AD. Petersen R C, *Mild cognitive impairment: transition between aging and Alzheimer's disease*, Neurology 15:93–101 (2000).

The apolipoprotein E gene (APOE) has consistently been found to be associated with both sporadic and familial AD. Saunders A M, Strittmatter W J, Schmechel D, St. George-Hyslop P H, Pericak-Vance M A, Joo S H, Rosi B L, Gusella J F, Crapper-MacLachlan D R, Alberts M J, Hulette C, Crain B, Goldgaber D, and Roses A D, *Association of apolipoprotein E allele epsilon 4 with late-onset familial and sporadic Alzheimer's disease*, Neurology 43:1467–1472 (1993); Poirier J, Davignon J, Bouthillier D, Kogan S, Bertrand P, and Gauthier S, *Apolipoprotein E polymorphism and Alzheimer's disease*, Lancet 342:697–699 (1993). However, using APOE genotyping to diagnose AD is limited due to the non-Mendelian relationship between APOE genotype and AD. In a large autopsy-based study, using APOE genotyping alone (presence or absence of an ∈4 allele) produced a 65% sensitivity and a 68% specificity. Mayeux R, Saunders A M, Shea S, Mirra S, Evans D, Roses A D, Hyman B T, Crain B, Tang M X, and Phelps C H, *Utility of the apolipoprotein E genotype in the diagnosis of Alzheimer's disease*, Alzheimer's disease centers consortium on apolipoprotein E and Alzheimer's disease, N Engl J Med 338:

506–511 (1998). In the same study, the sequential use of clinical diagnosis and APOE genotyping reduced the false positive rate of the clinical diagnosis, increased specificity from 55% to 84% and modestly increasing the positive predictive value from 90 to 94%. Mayeux R, *Evaluation and use of diagnostic tests in Alzheimer's disease*, Neurobiol Aging 19:139–143 (1998); Mayeux R, Saunders A M, Shea S, Mirra S, Evans D, Roses A D, Hyman B T, Crain B, Tang M X, and Phelps C H, *Utility of the apolipoprotein E genotype in the diagnosis of Alzheimer's disease*, Alzheimer's disease centers consortium on apolipoprotein E and Alzheimer's disease, N Engl J Med 338:506–511 (1998). Thus, while using APOE alone as a predictive test is not recommended, a testing strategy that combines APOE and another biomarker may well be beneficial. Roses A D. *Apoplipoprotein E genotyping in the differential diagnosis, not prediction, of Alzheimer's disease*, Ann Neurol 38:6–14 (1995).

Aging remains the greatest risk factor for AD, and changes in peripheral immune cell phenotype associated with aging have been documented in previous studies. For example, an increase in the ratio of memory to naïve CD4+T cells (indicated by an increase in the CD45RO/CD45RA ratio), which reflects an increase in the activation status of these cells, has been shown to correlate with aging. Flurkey K, Stadecker M, and Miller RA, *Memory T lymphocyte hyporesponsiveness to non-cognate stimuli: A key factor in age-related immunodeficiency*, Eur J Immunol 22:931–935 (1992); Utsuyama M, Hirokawa K, Kurashima C, Fukayama M, Inamatsu T, Suzuki K, Hashimoto W, and Sato K, *Differential age-change in the numbers of CD4+CD45RA and CD4+CD29+T cell subsets in human peripheral blood*, Mech Ageing Dev 63:57–68 (1992). Similar shifts in the numbers and activation status of circulating T cell subpopulations have been postulated to account for a dysfunctional immune response observed in the elderly and even more so in AD patients. Hu G R, Walls R S, Creasey H, McCusker E, and Broe G A, *Peripheral blood lymphocyte subset distribution and function in patients with Alzheimer's disease and other dementias*, Aust N Z J Med 25:212–217 (1995); Ikeda T, Yamamoto K, Takahashi K, and Yamada M, *Immune system-associated antigens on the surface of peripheral blood lymphocytes in patients with Alzheimer's disease*, Acta Psychiatr Scand 83:444–448 (1991).

SUMMARY OF THE INVENTION

The purpose and advantages of the present invention will be set forth in and apparent from the description that follows, as well as will be learned by practice of the invention. Additional advantages of the invention will be realized and attained by the methods particularly pointed out in the written description and claims hereof, as well as from the figures.

To achieve these and other advantages in accordance with the purpose of the invention, as embodied and broadly described, the invention includes a method of assessing the risk of developing, of diagnosing, or of measuring the progression of Alzheimer's disease in a patient comprising of obtaining a blood sample from a patient, determining CD45 isoform expression of blood cells contained in the blood sample, and relating the determined CD45 isoform expression to an assessment of the risk of developing the disease, a diagnosis of the disease, or a measure of the progression of the disease. The blood cells, for purposes of illustration and not limitation, may comprise monocytes, macrophages, lymphocytes, or a combination thereof. In a particular embodiment, the blood cells may comprise T cells, B cells, or a combination thereof.

The CD45 isoform may comprise CD45RA, CD45RO, or a combination thereof. The method of the invention may further comprise determining CD45 iso form expression by cytometric analysis, quantitative Western immunoblotting, or quantitative RT-PCR or a combination thereof. The method of the invention may even further comprise determining the APOE genotype or phenotype and relating that APOE genotype or phenotype to the determined CD45 isoform expression to arrive at an assessment of the risk of developing the disease, a diagnosis of the disease, or a measure of the progression of the disease.

Another aspect of the invention includes a method of assessing the cognitive status of a patient comprising of obtaining a blood sample from a patient, determining CD45 isoform expression of blood cells contained in the blood sample, and relating, the determined CD45 isoform expression to the cognitive status of the patient.

It is to be understood that both the foregoing general description and the following detailed description are exemplary and are intended to provide further explanation of the invention claimed.

The accompanying figures, which are incorporated in and constitute part of this specification, are included to illustrate and provide a further understanding of the methods and system of the invention. Together with the description, the drawings serve to explain the principles of the invention.

MATERIALS AND METHODS

Reference will now be made in detail to the present preferred embodiments of the invention, examples of which are illustrated in the accompanying figures.

The methods presented herein may be used for assessing the risk of developing, of diagnosing, or of measuring the progression of Alzheimer's disease in a patient comprising of obtaining a blood sample from a patient, determining CD45 isoform expression of blood cells contained in the blood sample, and relating the determined CD45 isoform expression to an assessment of the risk of developing the disease, a diagnosis of the disease, or a measure of the progression of the disease. The following, abbreviations are used in describing the invention: AD Prob. probable AD; ANOVA analysis of variance; APOE apolipoprotein E gene; CD cluster of differentiation; Cogn. Abn. cognitively abnormal individuals; MMSE Mini-Mental State Examination; NINCDS-ADRDA National Institute of Neurological and Communicative Disorders and Stroke/Alzheimer's Disease and Related Disorders Association criteria; Normal cognitively normal individuals; NPV negative predictive value; Other Dem. other dementia; PPV positive predictive value.

1) Participants

The sample was comprised of 192 individuals (90 cognitively normal, 37 cognitively abnormal, 46 diagnosed with probable AD (AD Prob.), and 19 with other dementias) from 31 states who were referred to the University of South Florida Memory Disorder Clinic or who were screened for cognitive disorder in the community by clinic staff. Those screened in the community were elderly volunteers who agreed to complete a MMSE questionnaire and donate a blood sample. Folstein M F, Folstein S E, and McHugh P R, *"Mini-mental state". A practical method for grading the cognitive state of patients for the clinician*, J Psychiatr Res 12:189–198 (1975). Of those screened in the community, 90 subjects scored 27 or greater on the MMSE and were thus considered cognitively normal (Normal, 40 male, mean age=75.54±7.52 SD, MMSE=29.0±1.12 SD). During cognitive screening, 37 participants scored ≦26 on the MMSE and were thus considered cognitively abnormal (Cogn. Abn., 19 male, mean age=77.29±10.59 SD, MMSE=20.6±6.39 SD). For those seen in the community screen, the presence of obvious depressive symptomatology was either ruled out during face-to-face clinical interview or with scores of less than 14 on a 17-item Hamilton Depression Scale.

Those seen and diagnosed with dementia in the clinic underwent extensive evaluation before a consensus diagnosis (involving all evaluating professionals) was made. Assessment generally included full medical and neurocognitive evaluation by a physician specialist in dementia, neuropsychological, and neuroradiological (magnetic resonance imaging analysis) assessment, with routine blood tests. Full details of this evaluation are available upon request. For this study, 46 cases were diagnosed as having probable AD (AD Prob., 10 male, mean age=75.47±6.81 SD, MMSE=16.8±5.5 SD) according to NINCDS-ADRDA criteria. In addition, patients with other dementia including frontotemporal dementia (n=2 females, diagnosed in accordance with consensus criteria,), dementia with Lewy Bodies (n=2 males and 1 female diagnosed in accordance with the consensus guidelines from the DLB International Workshop, and patients clinically diagnosed with stroke (n=10 male and 4 female, these individuals had an MMSE score of ≦22, impairment in more than 2 cognitive domains, and impaired independent activities of daily living); total n=19, 12 male, mean age=72.53±10.45 SD, MMSE=18.9±6.6 SD], were included as a non-AD demented sample. Neary D, Snowden J S, Gustafson L, Passant U, Stuss D, Black S, Freedman M, Kertesz A, Robert P H, Albert M, Boone K, Miller B L, Cummings J, and Benson D F, *Frontotemporal lobar degeneration: a consensus on clinical diagnostic criteria*, Neurology 51:1546–1554 (1998); McKeith I G, Galasko D, Kosaka K, Perry E K, Dickson D W, Hansen L A, Salmon D P, Lowe J, Mirra S S, Byrne E J, Lennox G, Quinn N P, Edwardson J A, Ince P G, Bergeron C, Bums A, Miller B L, Lovestone S, Collerton D, Jansen E N, Ballard C, de Vos R A, Wilcock G K, Jellinger K A, and Perry R H, *Consensus guidelines for the clinical and pathologic diagnosis of dementia with Lewy bodies (DLB): report of the consortium on DLB international workshop*, Neurology 47:1113–1124 (1996). Thus, the Normal and Cogn. Abn. groups were drawn from a community-based sample, while the AD Prob. and Other Dem. groups were sampled from the clinic setting.

None of the subjects exhibited symptoms of severe systemic infection when collecting blood. Controls and AD Prob. patients were all ≧60 years of age, and each group was not significantly different in age (by one-way ANOVA, p=0.296). The Normal, Cogn. Abn. and Other Dem. groups were not significantly different in gender (p=0.153), while AD Prob. patients significantly differed from the other groups in gender (p<0.01). However, no significant correlation existed between gender and any of the CD45 isoforms investigated (CD45RA, p=0.345; RB, p=0.389; RO, p=0.450; the CD45RO/RA ratio, p=0.589), suggesting that the gender difference did not affect analyses.

Western Immunoblotting

Leukocytes were isolated from whole, sodium heparin-treated blood samples (10 mL) using RBC lysis solution. Immediately following isolation, leukocytes were washed in ice-cold phosphate buffered saline (PBS) 3 times and lysed in an ice-cold lysis buffer containing 20 mM Tris-HCl (pH 7.5), 150 mM NaCl, 1 mM EDTA, 10% Triton X-100, 2.5 mM sodium pyrophosphate, 1 mM β-Glycerophosphate, 1 mM $Na_3VO_4$, 1 μg/mL Leupeptin, and 1 mM PMSF. After incubating for 30 minutes on ice, samples were centrifuged at high speed for 15 minutes, and supernatants were collected. Total protein content was estimated using the Bio-Rad protein assay (Bio-Rad, Hercules, Calif.). An aliquot corresponding to 50 μg of total protein of each sample was separated by SDS-PAGE and transferred electrophoretic ally to Immune Blot™ PVDF membranes (Bio-Rad, Hercules, Calif.). Nonspecific antibody binding was blocked with 5% non-fat dry milk for 1 h at room temperature in TBS (20 mM Tris, 500 mM NaCl, pH 7.5). Immunoblotting was carried out with a primary antibody (1:100 dilution, purified mouse anti-human anti-CD45, anti-CD45PA, or anti-CD45RO monoclonal antibodies, Santa Cruz Biotechnology, Inc., Santa Cruz, Calif.) followed by an anti-mouse alkaline phosphatase-conjugated IgG secondary antibody (1:1500 dilution, Santa Cruz Biotechnology, Inc., Santa Cruz, Calif.) as a tracer. The Immun-Star® chemiluminescent substrate (Bio-Rad, Hercules, Calif.) was used to develop the blots. The invention encompasses measuring CD45 isoforms by western immunoblots from various types of blood cells. The blood cells, for purposes of illustration and not limitation, may comprise monocytes, macrophages, lymphocytes, or combinations thereof. In a particular embodiment, the blood cells may comprise T cells, B cells, or a combination thereof. The CD45 isoform may comprise CD45RA, CD45RO, or a combination thereof.

Flow Cytometry

All PE- and FITC-conjugated monoclonal mouse anti-human antibodies (mAbs, mouse anti-CD45RA, anti-CD45RB, anti-CD45RO, anti-CD4, and IgG control antibodies) were purchased from PharMingen (Los Angeles, Calif.). To test the specificity of the anti-CD45RA and anti-CD45RO antibodies, flow cytometric analyses were performed on cultures of Jurkat T cells or CD45-deficient Jurkat T cells. Results showed that ~35% of Jurkat T cells stained positive for CD45RA, and >50% of these cells stained from CD45RO. Further, neither CD45RA nor CD45RO were detected on CD45-deficient Jurkat T cells. Twenty-four hours after collection, whole, sodium heparin-treated blood samples (200 μL) were double labeled with FITC-conjugated anti-CD4 and with PE-conjugated anti-CD45RA, anti-CD45RB or anti-CD45RO antibodies (1:20 dilution for each), Aliquots of each sample were also double labeled with FITC-conjugated and PE-conjugated mouse IgG (isotype-matched) control antibodies (1:20 dilution). Erythrocytes were then lysed in a red blood cell lysis solution (Gentra Systems, Minneapolis, Minn.), and samples were centrifuged and cell pellets suspended in 300 μL of a 10% formalin solution (Sigma) for 5 min. Cells were washed 3 times in PBS, then resuspended in 250 μL of flow buffer (PBS containing 0.1% sodium azide and 1.0% fetal bovine serum) for flow cytometric analysis, according to our previously described methods. Tan J, Town T, Paris D, Placzek A, Parker T, Crawford F, Yu H, Humphrey J, and Mullan M, *Activation of microglial cells by the CD40 pathway: relevance to multiple sclerosis*, J Neuroimmunol 97:77–85 (1999). 10,000 CD4+T cells were collected and analyzed by flow cytometry for each study participant to exclude the possibility that observed differences on CD45 isoform expression may be due to different numbers of CD4+T cells analyzed. Scatter plots and percentages of fluorescent events were generated using CellQuest flow cytometric analysis software (Becton Dickinson, San Jose, Calif.). Data are represented as the percentage of cells double positive for CD4 and the particular CD45 isoform minus the percentage of cells double positive for the isotype-matched control antibodies.

To ensure accurate flow cytometric analysis and protect against artifacts, the following additional steps were taken: To test the specificity of the anti-CD45RA and anti-CD45RO antibodies, flow cytometric analyses were performed on cultures of human Jurkat T cells or CD45-deficient Jurkat T cells. Results showed that ~35% of Jurkat T cells stained positive for CD45RA, and >50% of these cells stained for CD45RO. Furthermore, neither CD45RA nor CD45RO were detected on CD45-deficient Jurkat T cells. Titer curves were generated for each antibody from 1:50 to 1:400, and a 1:200 dilution was generally found to give the highest signal to noise ratio, thereby allowing the greatest discriminative ability between positive and negative cells. Furthermore, antibody aggregates were minimized by storing all antibodies at 4° C. and discarding antibodies after 6 months of storage, and cell death in sample preparations was minimized by keeping cells at 4° C. throughout the staining procedure and by supplementing flow buffer with 1.0% fetal bovine serum as described above.

Two different methods of flow cytometric analysis were conducted on the study data: The first method was to gate on all lymphocytes by forward and side-scatter criteria, and then to generate a 4-quadrant dot-plot. The upper-right quadrant percentage was then divided by the sum of the upper-right and lower-right quadrants, and subtracted from the figure obtained with the isotype-matched control antibodies, yielding percentage of CD4+lymphocytes that were double-positive for the CD45 isoform under consideration. In the second method, we gated on CD4+lymphocytes, and then simply generated histograms to determine percentage shift for CD45 isoforms by subtracting peak shifts from any shifts observed with the isotype-matched control antibody, again yielding, percentage of CD4 and CD45 isoform double-positive cells. Finding no significant differences (p>0.05) after statistically comparing the 2 methods, we adopted the more conventional 4-quadrant method. Finally, as we observed significant overlap between CD45RA-positive and CD45RO-positive CD4+T cells in our elderly cohort, to rule out possible methodological shortcomings that could yield this result, we examined these profiles in a small sample of healthy, young subjects (n=8, between 20 and 36 years of age). Consistent with the literature, we did not detect overlap between CD45/RA and CD45RO-positive CD4+T cells in any of these subjects (mean CD45RA+/CD4+T cells=32.42±1.79 SD; mean CD45RO+/CD4+T cells=66.34±1.95), suggesting that the observed overlap in our elderly subject cohort is valid. The invention encompasses measuring CD45 isoforms by flow cytometry from various types of blood cells. The blood cells, for purposes of illustration and not limitation, may comprise monocytes, macrophages, lymphocytes, or combinations thereof. In a particular embodiment, the blood cells may comprise T cells, B cells, or a combination thereof. The CD45 isoform may comprise CD45RA, CD45RO, or a combination thereof.

Statistical Analysis

All quantitative data were analyzed by the one-sample Kolmogorov-Smirnov test to determine if data were normally distributed. If data were normally distributed, one-way analysis of variance (ANOVA) followed by post hoc comparison using either Bonferroni's or Dunnett's T3 method (where Levene's test for homogeneity of the variance was used to determine the method of post hoc analysis) was used to analyze the data. If data was not normally distributed, the Kruskal-Wallis H test was followed by post hoc comparison using, the Mann-Whitney U test. Gender comparisons between-groups were performed using the likelihood ratio $\chi^2$ statistic, and age comparisons were performed using, one-way ANOVA. Bivariate correlations were determined by first rank-ordering data according to Spearman's method, and then determining Pearson's r with associated significance.

Sensitivity (percentage of the AD Prob. population positive for the test) and specificity (percentage of the non-AD Prob. population negative for the test) for APOE $\epsilon$4 (apolipoprotein E gene) were calculated based on 2-by-2 contingency tables, and Receiver Operator Characteristic (ROC) curve analysis was performed to determine these values for CD45 isoforms, both alone or when sequentially tested following APOE $\epsilon$4 genotyping as previously described. Mayeux R, Saunders A M, Shea S, Mirra S, Evans D, Roses A D, Hyman B T, Crain B, Tang M X, and Phelps C H, *Utility of the apolipoprotein E genotype in the diagnosis of Alzheimer's disease*, Alzheimer's disease centers consortium on apolipoprotein E and Alzheimer's disease, N Engl J Med 338:506–511 (1998). For ROC analyses, cutoff scores, sensitivity, and specificity for CD45RA levels or the CD45RO/RA ratio on CD4+T cells were determined based on the area under the curve. Positive predictive value (probability that an individual is actually diagnosed as AD Prob. when the test is positive) and negative predictive value (probability that a patient is truly not diagnosed as AD Prob. when the test is negative) were calculated as previously described. Saunders A M, *Specificity, sensitivity, and predictive value of apolipoprotein-E genotyping for sporadic Alzheimer's disease*, Lancet 348:90–93 (1996). Multiple hierarchical logistic regression models controlling for gender were used to assess predictive ability of APOE $\epsilon$4 and CD45 status (CD45RA or the CD45RO/RA ratio) when modeled alone or together. $R^2$ values were calculated according to Nagelkerke's method, and likelihood ratio testing was used to make between-models comparisons. For all analyses, alpha levels were set at 0.05, and SPSS software release 10.0.5 was used.

Results

Figure 1:
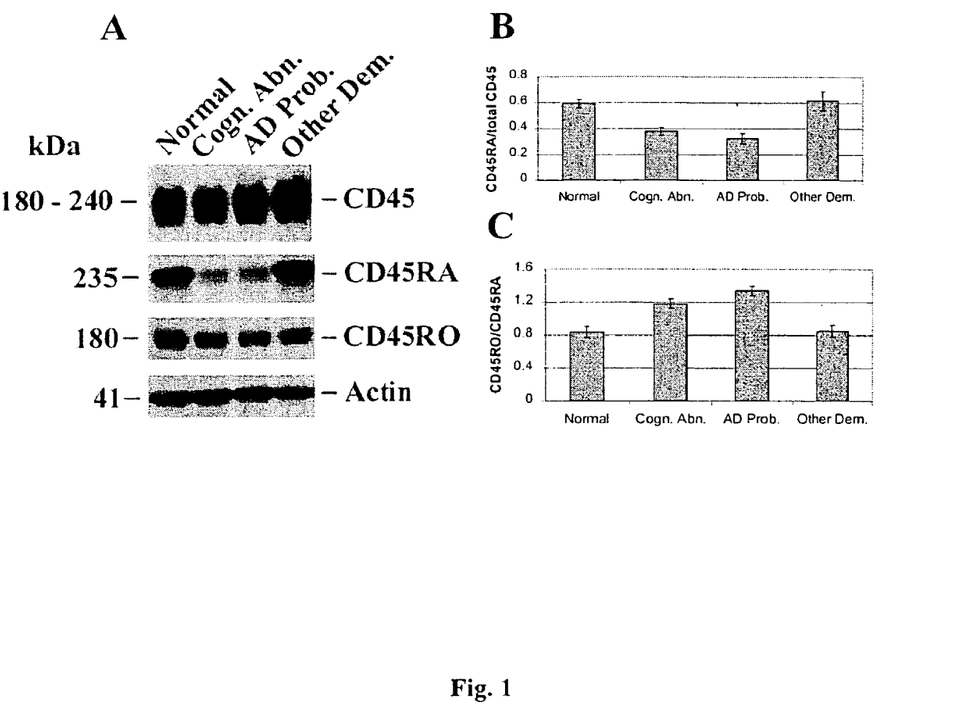
FIGS. 1A–C: Differential expression of CD45 isoforms in leukocytes from AD patients and cognitively abnormal participants compared to controls.

Probable AD patients and cognitively abnormal individuals exhibited reduced CD45RA expression and elevated CD45RO/RA ratio in leukocytes:

FIGS. 1 (A), (B), and (C) show differential expression of CD45 isoforms in leukocytes from AD patients and cognitively abnormal participants compared to controls. In order to determine whether expression levels of CD45RO and/or CD45RA are altered in AD patients compared to controls, Western immunoblotting were performed on total peripheral leukocytes isolated from 10 subjects randomly selected from each study group (FIG. 1A). FIG. 1(A) is a representative Western blot showing a decrease in CD45RA expression in both AD Prob. cases and Cogn. Abn. subjects compared to normal individuals or Other Dem. patients.

Total CD45 was used as an internal reference for semi-quantitative measurement of CD45 isoform expression by densitometric analysis shown in Fig. 1 (B) and (C). FIG. 1(B) Graph shows the band density ratio of CD45RA to total CD45 (mean±1 SEM, n=10 for each group). Fig. 1(C) Graph shows the band density ratio of CD45RO/CD45RA (mean±1 SEM, n=10 for each group). Figure 1(B) shows statistically significant between-groups differences (p<0.001) and post-hoc comparison showed significant differences (p<0.001) in AD Prob. or Cogn. Abn. individuals compared to normal. No significant differences were observed between normal subjects and Other Dem. patients (p>0.05).

In evaluating the CD45RO/CD45RA ratio in peripheral leukocytes, Fig 1(C) data shows a statistically significant (p<0.001) elevation of CD45RO/CD45RA ratio in both AD Prob. patients and Cogn. Abn. individuals as compared to Normals, who did not significantly differ from Other Dem. patients. These data led us to specifically evaluate expression levels of CD45 isoforms on CD4+T cells, the specific cell type where differential expression of CD45 isoforms have been shown to be a marker of immune memory and cellular activation. Flurkey K, Stadecker M, and Miller R A, *Memory T lymph ocyte hyporesponsiveness to non-cognate stimuli: A key factor in age-related immunodeficiency*, Eur J Immunol 22:931–935 (1992); Utsuyama M, Hirokawa K, Kurashima C, Fukayama M, Inamatsu T, Suzuki K, Hashimoto W, and Sato K, *Differential age-change in the numbers of CD4+CD45RA and CD4+CD29+T cell subsets in human peripheral blood*, Mech Ageing Dev 63:57–68 (1992); Hu G R, Walls R S, Creasey H, McCusker E, and Broe G A, *Peripheral blood lymphocyte subset distribution and function in patients with Alzheimer's disease and other dementias*, Aust N Z J Med 25:212–217 (1995); Ikeda T, Yamamoto K, Takahashi K, and Yamada M, *Immune system-associated antigens on the surface of peripheral blood lymphocytes in patients with Alzheimer's disease*, Acta Psychiatr Scand 83:444–448 (1991). The invention encompasses measuring CD45 isoforms by western immunoblots from various types of blood cells. The blood cells, for purposes of illustration and not limitation, may comprise monocytes, macrophages, lymphocytes, or combinations thereof. In a particular embodiment, the blood cells may comprise T cells, B cells, or a combination thereof. The CD45 isoform may comprise CD45RA, CD45RO, or a combination thereof.

Figure 2:
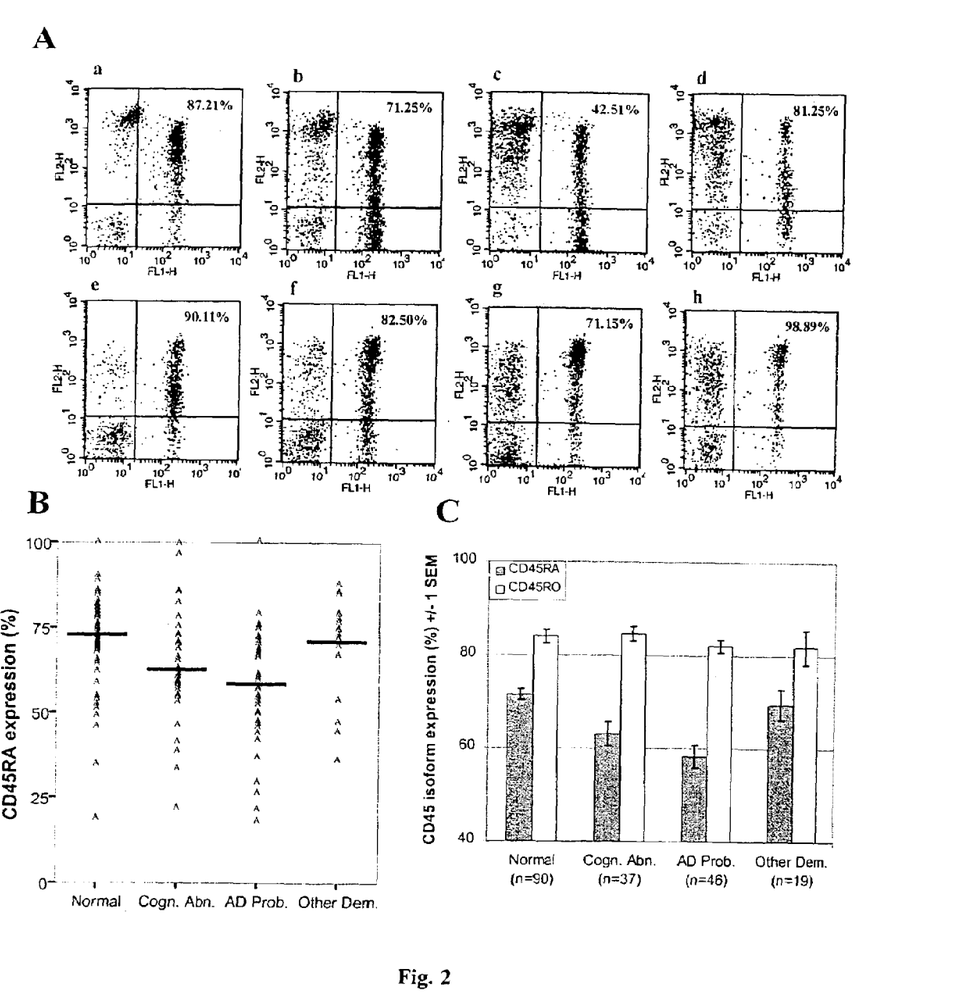
FIGS. 2A–C: CD4+T cells from probable AD patients and cognitively abnormal participants showing altered CD45RA isoform expression profiles compared to controls.

Probable AD Patients and Cognitively Abnormal Individuals Exhibited Decreased CD45RA and Increased CD45RO/RA Ratio on CD4+T Cells:

FIGS. 2 (A), (B), and (C) show that CD4+T cells from probable AD patients and cognitively abnormal participants have altered CD45RA isoform expression profiles compared to controls. CD4+T cell subsets from Normals, Cogn. Abn. individuals, AD Prob. cases and Other Dem. patients were examined by flow cytometry (FIG. 2A). FIG. 2(A) shows FACS dot-plots of representative samples indicating differential expression of CD45 isoform is on CD4+T cells (row a, CD45RA; row b, CD45RO) from normal subjects (column a, e), Cogn. Abn. participants (column b, f), AD Prob. patients (column c, g) and Other Dem. patients (column d, h). The x-axis (FL1-H) represents log fluorescence intensity of the FITC-conjugated anti-CD4 mAb, and the y-axis (FL2-H) represents log fluorescence intensity of the PE-conjugated anti-CD45 mAb. The upper right-hand portion of the plot indicates double-positive cells for CD4 and CD45RA or CD45RO.

FIG. 2(B) shows the distribution of the percentage of CD45RA positive CD4+T cells. FIG. 2(B) Scatterplot shows the percentage of CD45RA positive CD4+T cells. The means are represented as a solid bar.

FIG. 2 (C) shows that percentages of CD45RA-expressing CD4+T cells were significantly (p<0.001) decreased in AD Prob. and Cogn. Abn. subjects compared to Normal individuals. FIG. 2 (C) also shows significant differences were detected between any of the subject groups on CD45RO-expressing CD4+T cells. FIG. 2(C) Graph summarizes expression levels (%) of CD45RA and CD45RO (mean±1 SEM; n=90 for Normals; n=37 for Cogn. Abn.; n=46 for AD Prob.; n=19 for Other Dem.). Percentage of CD45 iso form expression was calculated by subtracting the mean fluorescence value for the isotype-matched control mAb from the mean fluorescence value of the CD45 isoform-specific mAb. For CD45RA, Kruskal Wallis H testing, revealed significant between-groups differences (p<0.001), and post hoc comparison revealed significant differences between Normal participants and either AD Prob. patients or Cogn. Abn. individuals (p<0.001), but not between Other Dem. subjects and Normals (p>0.05). No significant between-groups differences were observed on CD45RO status (p>0.05). mAb, monoclonal antibody.

Figure 3:
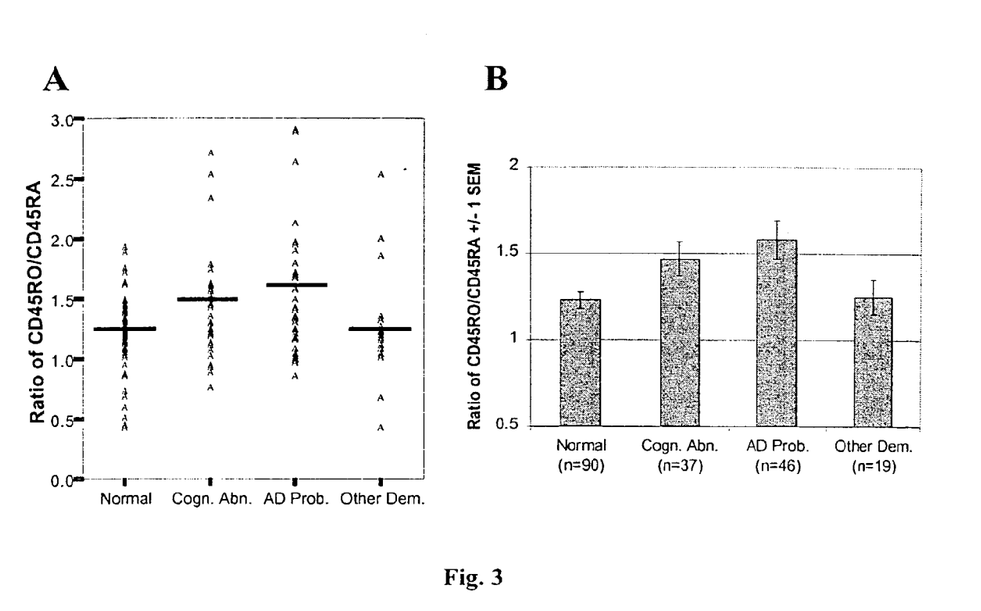
FIGS. 3A–B: CD4+T cells from probable AD patients and cognitively abnormal participants showing an altered ratio of CD45RO/CD45RA compared to controls.

FIGS. 3 (A) and (B) show that CD4+T cells from probable AD patients and cognitively abnormal participants have an altered ratio of CD45RO/CD45RA compared to controls. FIG., 3 (A) is a scatterplot showing the ratio of CD45RO/CD45RA on CD4+T cells. The means are represented as a solid bar. FIG. 3 (B) Graph summarizes the ratio of CD45RO/CD45RA expression levels shown in (A) (mean±1 SEM; n=90 for Normals; n=37 for Cogn. Abn.; n=46 for AD Prob.; n=19 for Other Dem.). Kruskal Wallis H testing revealed significant between-groups differences (p=0.001), and post hoc comparison revealed significant differences between Normal participants and either AD Prob. patients or Cogn. Abn. individuals (p<0.01). No significant difference was observed between Other Dem. subjects and Normals (p>0.05).

When considering the ratio of CD45RO/CD45RA expression on CD4+T cells, this ratio was significantly (p<0.01) increased in both AD Prob. and Cogn. Abn. patients compared to Normals, suggesting an increase in the CD4+T cell memory phenotype in these individuals (scatterplot, FIG. 3A; summary data, FIG. 3B). When considering CD45PA or the CD45RO/CD45RA ratio on CD4+T cells, no significant differences were observed between Other Dem. subjects and Normal participants. Additionally, when examining CD45RB isoform expression on CD4+T cells by this method, no significant differences were found between subject groups (p>0.05, data not shown). A previous study found that CD45R isoforms were decreased on CD4+T cells in patients diagnosed with probable AD, although those authors were not able to identify the specific isoforms responsible for this effect. Ikeda T, Yamamoto K, Takahashi K, and Yamada M, *Immune system-associated antigens on the surface of peripheral blood lymphocytes in patients with Alzheimer's disease*, Acta Psychiatr Scand 83:444–448 (1991). Data now show that CD45RA, not CD45RO or CD45RB, is specifically decreased on CD4+T cells in AD Prob. patients and Cogn. Abn. individuals.

Evaluation of CD45 Isoform Alteration on CD4+T Cells as a Biomarker for Probable AD:

For a biomarker of AD to be useful, it must be sensitive, specific, and have positive predictive value (PPV) and negative predictive value (NPV). Saunders A M, Strittmatter W J, Schmechel D, St. George-Hyslop P H, Pericak-Vance M A, Joo S H, Rosi B L, Gusella J F, Crapper-MacLachlan D R, Alberts M J, Hulette C, Crain B, Goldgaber D, and Roses A D, *Association of apolipoprotein E allele epsilon 4 with late-onset familial and sporadic Alzheimer's disease*, Neurology 43:1467–1472 (1993); Mayeux R, Saunders A M, Shea S, Mirra S, Evans D, Roses A D, Hyman B T, Crain B, Tang M X, and Phelps C H, *Utility of the apolipoprotein E genotype in the diagnosis of Alzheimer's disease, Alzheimer's disease centers consortium on apolipoprotein E and Alzheimer's disease*, N Engl J Med 338:506–511 (1998). Thus, we evaluated CD45RA and the CD45RO/CD45RA ratio for sensitivity, specificity, PPV and NPV. In addition, we genotyped our study subjects for APOE $\epsilon$4, a known diagnostic marker of AD according to previously published methods. Mayeux R, *Evaluation and use of diagnostic tests in Alzheimer's disease*, Neurobiol Aging 19:139–143 (1998); Mayeux R, Saunders A M, Shea S, Mirra S, Evans D, Roses A D, Hyman B T, Crain B, Tang M X, and Phelps C H, *Utility of the apolipoprotein E genotype in the diagnosis of Alzheimer's disease*, Alzheimer's disease centers consortium on apolipoprotein E and Alzheimer's disease. N Engl J Med 338:506–511 (1998); Roses A D, *Apoplipoprotein E genotyping in the differential diagnosis, not prediction, of alzheimer's disease*, Ann Neurol 38:6–14 (1995); Wenham P R, Price W H, and Blandell G, *Apolipoprotein E genotyping by one-stage PCR*, Lancet 337:1158–1159 (1991). This enabled us to compare sensitivity, specificity, PPV, and NPV for CD45RA and to compare CD45RO/CD45RA ratio to APOE $\epsilon$4 and determine if testing for APOE $\epsilon$4 followed by CD45RA or the CD45RO/CD45RA ratio might increase these measures over APOE $\epsilon$4 alone. The sensitivity, specificity, PPV, and NPV values for APOE $\epsilon$4 for predicting AD were similar to previously published data. Mayeux R, *Evaluation and use of diagnostic tests in Alzheimer's disease*, Neurobiol Aging 19:139–143 (1998); Mayeux R, Saunders A M, Shea S, Mirra S, Evans D, Roses A D, Hyman B T, Crain B, Tang M X, and Phelps C H, *Utility of the apolipoprotein E genotype in the diagnosis of Alzheimer's disease*, Alzheimer's disease centers consortium on apolipoprotein E and Alzheimer's disease, N Engl J Med 338:506–511 (1998); Roses A D, *Apoplipoprotein E genotyping, in the differential diagnosis, not prediction, of Alzheimer's disease*, Ann Neurol 38:6–14 (1995); Saunders A M, *Specificity, sensitivity, and predictive value of apolipoprotein-E genotyping for sporadic Alzheimer's disease*, Lancet 348:90–93 (1996).

Table 1, shown below, demonstrates the validity of APOE $\epsilon$4, CD45 isoforms, and the sequential test. Sensitivity, specificity, PPV, and NPV were calculated as described in Methods, and the sequential test refers to APOE genotyping followed by CD45 isoform expression. level testing. Values were obtained by comparing AD Prob. patients to all other subjects but Cogn. Abn. individuals; however, similar figures were obtained when grouping AD Prob. and Cogn. Abn. subjects together.

CD45RA and CD45RO/RA ratio measurements, alone or when sequentially tested, increased sensitivity, PPV, and NPV compared to APOE $\epsilon$4 alone while maintaining specificity comparable to that of APOE $\epsilon$4 (Table 1). Specifically, CD45RA measurement showed the largest increase. Furthermore, following APOE $\epsilon$4 testing, with CD45RA or the CD45RO/CD45RA ratio increased sensitivity, PPV, and NPV compared to APOE $\epsilon$4 alone while maintaining specificity comparable to that of APOE $\epsilon$. Increases in sensitivity, PPV, and NPV values are most pronounced when considering APOE $\epsilon$4 together with CD45RA. Table 1 data thereby shows that CD45 isoform measures provide additional information for predicting, diagnosing or treating, AD.

TABLE 1

Validity of APOE $\epsilon$4, CD45 isoforms, and the sequential test

|  | Cutoff | Sensitivity | Specificity | PPV | NPV |
| --- | --- | --- | --- | --- | --- |
| APOE $\epsilon$4 | ≧$\epsilon$4 | .51 | .71 | .46 | .75 |
| CD45RA | 68.14 | .76 | .70 | .55 | .86 |
| APOE $\epsilon$4 + CD45RA | 63.90 | .82 | .73 | .80 | .79 |
| CD45RO/RA | 1.21 | .68 | .61 | .54 | .81 |
| APOE $\epsilon$4 + CD45RO/RA | 1.22 | .74 | .69 | .68 | .78 |

To further confirm that CD45RA or the CD45RO/CD45RA ratio are valuable biomarkers of probable AD, multiple hierarchical logistic regression models were employed, as shown in Table 2 below. Table 2 demonstrates predictive ability of APOE $\epsilon$4 and CD45 isoforms. Multiple hierarchical logistic regression models were carried out as described in Methods, and model summary data are displayed. Values were obtained by comparing AD Prob. patients to all other subjects but Cogn. Abn. individuals; however, similar figures were obtained when grouping AD Prob. and Cogn. Abn. subjects together. Class Predictions and $R^2$ values for CD45RA or the CD45RO/CD45RA ratio when modeled alone increased, compared to APOE $\epsilon$4 alone, suggesting, that CD45 isoforms are a better predictor of disease than APOE $\epsilon$4. Likelihood Ratio testing between models shows that CD45RA or the CD45RO/RA ratio, when modeled together with APOE $\epsilon$4, add significantly more predictive information than APOE $\epsilon$4 when modeled alone, as indicated by the significant p values shown. *$^{x-y}$ denotes comparison of model x to model y by Likelihood Ratio testing.

CD45RA and the CD45RO/CD45RA ratio are better predictors of disease than APOE $\epsilon$4, with CD45RA measurement showing, the greatest predictive ability, as indicated by increased class prediction and $R^2$ values compared to APOE $\epsilon$4. Additionally, when CD45RA or the CD45RO/CD45RA ratio are modeled together with APOE $\epsilon$4, class prediction and $R^2$ values are increased compared to APOE $\epsilon$4 alone, and likelihood ratio testing between models indicates that CD45RA or the CD45RO/CD45RA ratio in combination with APOE $\epsilon$4 are significantly adding more predictive information for disease than APOE $\epsilon$4 alone. Again, this effect is most pronounced when considering the APOE $\epsilon$4 and CD45RA combination.

TABLE 2

Predictive ability of APOE $\epsilon$4 and CD45 isoforms

| Model/description | Class Prediction | $R^2$ | df | P |
| --- | --- | --- | --- | --- |
| 0:$\beta_0$ | — | — | — | — |
| 1:$\beta_0$ + APOE $\epsilon$4 $\beta_1$ | 68.4% | .139 | 2 | =.001 |
| 2:$\beta_0$ + CD45RA $\beta_1$ | 75.5% | .277 | 2 | <.001 |
| 3:$\beta_0$ + APOE $\epsilon$4 $\beta_1$ + CD45RA $\beta_2$ | 75.2% | .304 | 3 | <.001 |
|  | — | — | 1 | *<.0001$^{3-1}$ |
| 4:$\beta_0$ + CD45RO/RA $\beta_1$ | 74.2% | .175 | 2 | <.001 |
| 5:$\beta_0$ + APOE $\epsilon$4 $\beta_1$ + CD45RO/RA $\beta_2$ | 75.2% | .218 | 3 | <.001 |
|  | — | — | 1 | *<.01$^{5-1}$ |

Discussion

Changes in peripheral immune cell phenotypes, including increases in the ratio of circulating memory vs. naïve T cells and changes in T cell activation and number are linked with aging and even more so with AD. Flurkey K, Stadecker M, and Miller R A, *Memory T lymphocyte hyporesponsiveness to non-cognate stimuli: A key factor in age-related immunodeficiency*, Eur J Immunol 22:931–935 (1992); Utsuyama M, Hirokawa K, Kurashima C, Fukayama M, Inamatsu T, Suzuki K, Hashimoto W, and Sato K, *Differential age-change in the numbers of CD4+CD45RA and CD4+CD29+T cell subsets in human peripheral blood*, Mech Ageing Dev 63:5 7–68 (1992); Hu G R, Walls R S, Creasey H, McCusker E, and Broe G A, *Peripheral blood lymphocyte subset distribution and function in patients with Alzheimer's disease and other dementias*, Aust N Z J Med 25:212–217 (1995); Ikeda T, Yamamoto K, Takahashi K, and Yamada M, *Immune system-associated antigens on the surface of peripheral blood lymphocytes in patients with Alzheimer's disease*, Acta Psychiatr Scand 83:444–448 (1991). These references suggest that AD patients have dysfunctional peripheral immune response, and we evaluated whether CD45 isoform alteration on CD4+T cells might be a valuable, simple, and minimally invasive biomarker for the disease. Results show that CD4+T cell CD45 isoform alteration (in particular CD45RA) is a valuable biomarker of clinically diagnosed AD. Furthermore, combination of CD45 isoform alteration with APOE ε4 genotyping results in additional predictive value. Finally, this strategy allows for the identification of individuals who are cognitively abnormal, many of whom later progress to AD. Petersen R C, *Mild cognitive impairment: transition between aging and Alzheimer's disease*, Neurology 15:935–101(2000).

Previous studies have shown that the CD45RO/CD45RA ratio on CD4+T cells increases with aging, indicating greater numbers of memory T cells in the elderly. Flurkey K, Stadecker M, and Miller R A, *Memory T lymphocyte hyporesponsiveness to non-cognate stimuli: A key factor in age-related immunodeficiency*, Eur J Immunol 22:931–935 (1992); Utsuyama M, Hirokawa K, Kurashima C, Fukayama M, Inamatsu T, Suzuki K, Hashimoto W, and Sato K, *Differential age-change in the numbers of CD4+CD45RA and CD4+CD29+T cell subsets in human peripheral blood*, Mech Ageing, Dev 63:57–68 (1992). Our data are in accordance with previous, as we find a modest but statistically significant positive correlation of the CD45RO/CD45RA ratio on CD4+T cells with age (r=0.170, p<0.05). After discovering that CD45 isoforms were markers of probable AD and cognitive abnormality, we further assessed a possible correlation between CD45 isoforms and Mini-Mental State Examination (MMSE) score: we found a significant negative correlation when including all subjects between the CD45RO/CD45RA ratio on CD4+T cells and MMSE score (r=−0.222, p<0.01), as well as a significant positive correlation between CD45RA on CD4+T cells and MMSE score (r=0.313, p<0.001). Folstein M F, Folstein S E, and McHugh P R, *"Mini-Mental state". A practical method for grading the cognitive state of patients for the clinician*, J Psychiatr Res 12:189–198 (1975). Mild cognitive impairment has been suggested to be an early stage of AD and our finding that differential CD45 isoform expression is a predictor of cognitive abnormality raises the possibility that CD45 isoform alteration CD4+T lymphocytes may be a biomarker for cognitive abnormality prior to diagnosis of AD. Petersen R C, *Mild cognitive impairment: transition between aging and Alzheimer's disease*, Neurology 15:93–101 (2000) Additionally, as 95% of patients who are clinically diagnosed with probable AD and who are subsequently brought to autopsy have pathologically confirmed AD, our results raise the possibility that differential CD45 isoform expression may be a valuable marker of post-mortem-confirmed AD. Price B H, Gurvit H, Weintraub S, Geula C, Leimkuhler E, and Mesulam M, *Neuropsychological patterns and language deficits in 20 consecutive cases of autopsy-confirmed Alzheimer's disease*, Arch Neurol 50:931–937 (1993).

Several possibilities account for the observation that differential CD45 isoform expression on CD4+T cells predicts probable AD. For example, it is possible that during the course of the disease, a soluble factor is released from the dysfunctional AD blood-brain barrier, and that this factor interacts with circulating T cells, producing a variation in CD45 expression. Kalaria R N, *Cerebrovascular degeneration is related to amyloid-beta protein deposition in Alzheimer's disease*, Ann N Y Acad Sci 826:263–271 (1997); Skoog I, Wallin A, Fredman P, Hesse C, Aevarsson 0, Karlsson I, Gottfries C G, and Blennow K, *A population study on blood-brain barrier function in 85-year–olds: relation to Alzheimer's disease and vascular dementia*, Neurology 50:966–971 (1998).] It is also possible that cell surface markers expressed on endothelial cells lining cerebral vessels in AD brain interact with passing T cells, a phenomenon referred to as T cell rolling, resulting in differential CD45 isoform expression on these cells. Hunt S W 3rd, Harris E S, Kellermann S A, and Shimizu Y, *T-lymphocyte interactions with endothelium and extracellular matrix*, Crit Rev Oral Biol Med 7:59–86 (1996). Whereas the above explanations rely on immune cross-talk between the CNS and the periphery, it is also possible that peripheral immunity, independent of the CNS, cause the alterations in CD45 isoform status. Finally, CD45 isoform alteration on CD4+T cells may be a result of other changes that co-occur with AD, such as weight loss, poor nutritional status, and decreased energy expenditure. Poehlman E T, and Dvorak R V, *Energy expenditure, energy intake, and weight loss in Alzheimer disease*, Am J Clin Nutr 71:650S–655S (2000). It should be noted that, while this study did not aim to address such etiological issues, additional studies designed to identify the causes and molecular mechanisms of these variations may provide indirect information about the etiology of the disease and aid in explaining why these changes appear to be specific to AD. In particular, we would like to examine the correlation between CD45 isoform alteration and neuropathologic or clinico-neuropathologic diagnosis of AD, to explore the relationship between aberrant CD45 isoform alteration in cognitively abnormal individuals and later diagnosis of AD, and to perform a prospective study in normal aging individuals to determine whether CD45 iso form alteration is a predictor of subsequent cognitive impairment and AD. Such studies will allow for determination of whether CD45 isoforms may be etiologically involved in dementia, markers of some other process that causes dementia, or are an epiphenomenon related to some other condition co morbid with dementia such as disability, nutrition, or infection. Additionally, these future studies will address whether CD45 isoform testing will be a good biomarker for dementia in patients before they become demented, during the preclinical phases of dementia, or in patients with mild cognitive impairment where diagnosis is most difficult.

It will be apparent to those skilled in the art that various modifications and variations can be made in the methods of the present invention without departing, from the spirit or scope of the invention. Thus, it is intended that the present invention include modifications and variations that are within the scope of the appended claims and their equivalents.

The invention claimed is:

1. A method of assessing the risk of developing and of diagnosing Alzheimer's disease in a patient comprising:
   (i) obtaining a blood sample from a patient;
   (ii) determining CD45RA and CD45RO expression of T cells contained in the blood sample; and
   (iii) relating the determined CD45RA and CD45RO expression to an assessment of the risk of developing the disease or a diagnosis of the disease,
   wherein a decreased CD45RO/RA expression and an increased CD45RO/RA ratio compared to control subjects indicates a risk of developing Alzheimer's disease or a diagnosis of Alzheimer's disease.

2. The method of claim 1 in which CD45RA and CD45RO expression is determined by cytometric analysis, Western blot, RT-PCR, or a combination thereof.

3. The method of claim 1, which is directed to assessing the risk of developing the disease.

4. The method of claim 1, which is directed to diagnosing the disease.

5. The method of claim 1, further comprising:
   determining an APOE $\epsilon$4 genotype in a patient; and
   relating the presence of the APOE $\epsilon$4 genotype biomarker to the determined CD45RA and CD45RO expression in the patient, wherein the finding that the patient has the APOE $\epsilon$4 genotype and has a decreased expression of CD45RA and an increased CD45RO/CD45RA ratio compared to control subjects increases the sensitivity, positive predictive value and negative predictive value of assessing the risk of developing and diagnosing Alzheimer's disease as compared to determining the APOE $\epsilon$4 genotype of the patient alone.

* * * * *

UNITED STATES PATENT AND TRADEMARK OFFICE
CERTIFICATE OF CORRECTION

PATENT NO. : 7,052,852 B1  Page 1 of 1
APPLICATION NO. : 10/426301
DATED : May 30, 2006
INVENTOR(S) : Mullan et al.

It is certified that error appears in the above-identified patent and that said Letters Patent is hereby corrected as shown below:

Column 15, Line 11, "CD45RO/RA" should read -- CD45RA/CD45RO --

Signed and Sealed this

Twenty-eighth Day of November, 2006

JON W. DUDAS
*Director of the United States Patent and Trademark Office*